United States Patent
Hata et al.

(10) Patent No.: US 11,090,233 B2
(45) Date of Patent: Aug. 17, 2021

(54) TITANIUM DIOXIDE POWDER AND POWDER COSMETIC INCORPORATING SAME

(71) Applicant: SHISEIDO COMPANY, LTD., Tokyo (JP)

(72) Inventors: Hideo Hata, Yokohama (JP); Motoharu Kimura, Yokohama (JP)

(73) Assignee: SHISEIDO COMPANY, LTD, Tokyo (JP)

( * ) Notice: Subject to any disclaimer, the term of this patent is extended or adjusted under 35 U.S.C. 154(b) by 125 days.

(21) Appl. No.: 16/625,252

(22) PCT Filed: May 29, 2018

(86) PCT No.: PCT/JP2018/020372
§ 371 (c)(1),
(2) Date: Dec. 20, 2019

(87) PCT Pub. No.: WO2019/003754
PCT Pub. Date: Jan. 3, 2019

(65) Prior Publication Data
US 2020/0146946 A1 May 14, 2020

(30) Foreign Application Priority Data
Jun. 26, 2017 (JP) .............................. JP2017-124517

(51) Int. Cl.
*A61K 8/02* (2006.01)
*A61K 8/19* (2006.01)
*A61K 8/25* (2006.01)
*A61K 8/29* (2006.01)
*A61Q 1/02* (2006.01)
*A61Q 1/12* (2006.01)

(52) U.S. Cl.
CPC .............. *A61K 8/022* (2013.01); *A61K 8/19* (2013.01); *A61K 8/25* (2013.01); *A61K 8/29* (2013.01); *A61Q 1/02* (2013.01); *A61Q 1/12* (2013.01)

(58) Field of Classification Search
None
See application file for complete search history.

(56) References Cited

FOREIGN PATENT DOCUMENTS

| EP | 3395764 A1 | 10/2018 |
|---|---|---|
| JP | H 10-245228 | 9/1998 |
| JP | 2000-191325 | 7/2000 |
| JP | 2006-265134 | 10/2006 |
| JP | 2010-24189 | 2/2010 |
| JP | 2010-173863 | 8/2010 |
| JP | 2013-227207 | 11/2013 |
| WO | WO2011/077084 A1 | 6/2011 |

OTHER PUBLICATIONS

EP 18824975.9, Extended European Search Report dated Feb. 22, 2021, 7 pages—English.
The structure, composition, and dimensions of $TiO_2$ and ZnO nanomaterials in commercial sunscreens, by Lewicka, Benolt, Yu, Benedetto, Fortner and Colvin, published Jul. 21, 2011, Journal of Nanopartical Research An Interdisciplinary Forum for Nanoscale Science and Technology, Kluwer Academic Publishers, vol. 13, No. 9, Springer Science+Business Media B.V. 2011, J. Nanopart Res (2011) 13:3607-3617—11 pages—English.
PCT/JP2018/020372, ISR and Written Opinion dated Aug. 21, 2018, 5 pages—Japanese, 2 pages—English.

*Primary Examiner* — Nannette Holloman
(74) *Attorney, Agent, or Firm* — Andrew F. Young, Esq.; Nolte Lackenbach Siegel

(57) ABSTRACT

A powder cosmetic provides an excellent finish and has an excellent usability while maintaining a hiding power, and exhibits an excellent capacity to be more transmissive of light in long wavelength regions (selective red light transmission capacity). The titanium dioxide powder is particles in which the apparent average particle diameter is 100 nm or more and less than 500 nm, the average crystallite diameter measured by x-ray diffraction is 15-30 nm, the specific surface area of 10-30 m2/g, and a ratio between the long diameter and short diameter of the shape (long diameter/short diameter) of 1.0-2.5, and the particles have a shape in which radially projecting needle-shaped projections are aggregated. The powder cosmetic incorporates the titanium dioxide powder.

10 Claims, 5 Drawing Sheets

Apparent average particle size = (major axis + minor axis)/2

TITANIUM DIOXIDE POWDER AND POWDER COSMETIC INCORPORATING SAME

CROSS REFERENCE TO RELATED APPLICATIONS

This application relates to and claims priority as a § 371 national phase, from PCT/JP2018/020372 filed May 28, 2018, the entire contents of which are incorporated herein by reference. This application also claims the priority of Japanese Patent Application No. 2017-124517, filed on Jun. 26, 2017, the disclosure of which is incorporated herein by reference in its entirety.

FIELD OF THE INVENTION

The present invention relates to a titanium dioxide powder and a powder cosmetic blended with the same, and particularly to a powder cosmetic which is excellent in makeup finish and texture, and has an excellent function of transmitting more light in a long wavelength region (red light selective transmission function) while a concealing ability is maintained.

BACKGROUND OF THE INVENTION

Titanium dioxide has a high-refractive index and excellent whiteness, concealing ability, and coloring ability, and has therefore been widely used as a white pigment for such as paints and plastics. Furthermore, titanium dioxide can also be used for cosmetics and catalysts as a substance for shielding (blocking) ultraviolet lights, such as ultraviolet light absorbers or ultraviolet light shielding agents, by controlling the particle size or photoactivity thereof. For that reason, in recent years, research and development has been actively conducted on such use of titanium dioxide.

It has been known that when a titanium dioxide powder having an apparent specific average particle size, which is formed of small spherical particles of a titanium dioxide having a specific average primary particle size and a spherical moss-like shape made up of a large number of titanium dioxide, is used for cosmetics, the titanium dioxide powder serves as a functional material capable of imparting a good slipperiness and excellent light resistance that conventional titanium dioxides do not have (Patent Literature 1).

Further, a cosmetic for lips comprising 1 to 15% by mass of rutile titanium dioxide aggregated particles having an average particle size of 0.2 to 0.4 μm and an average coefficient of friction (MIU value) of 0.4 to 0.6, and 1 to 40% by mass of semisolid oil has been known to give gloss, suppress noticeableness of wrinkles of lips, and provide excellent long-lasting makeup properties (Patent Literature 2).

Moreover, it has been known that a cosmetic containing a coloring material having a small absorbance of light on a long wavelength side (wavelength of 630 to 700 nm) in a visible light region makes a light transmitting property inside of skin close to bare skin, and thus a natural makeup finish can be achieved (Patent Literature 3).

As described above, as the titanium dioxide having an improved light transmittance for light on the long wavelength side, a rutile titanium dioxide, in form of thin strips or straw bundles has been developed. It has a particulate form of which rod-shaped particles are orientated and aggregated in bundles, and an apparent average length of the orientated and aggregated particle is 80 to 300 nm, an apparent average width of the orientated and aggregated particle is 30 to 150 nm, an apparent average axial ratio represented by the apparent average length/the apparent average width is 1.1 to 4, and a specific surface area is 120 to 180 m$^2$/g. This titanium dioxide has been known to have a high-level of transparency and ultraviolet light shielding ability (Patent Literature 4).

However, because this titanium dioxide is an aggregate of rod-shaped particles and has many voids in the secondary aggregate, the titanium dioxide has a lowered apparent refractive index and thus the concealing ability is insufficient when it is actually added to cosmetics. Furthermore, because the titanium dioxide is intended mainly for ultraviolet protection, the secondary aggregate has an apparent particle size of less than 100 nm that is clearly smaller than the particle size capable of maximizing the scattering effect of the titanium dioxide based on Mie theory, and this is also a factor making the concealing ability low.

A solid powder cosmetic represented by a powdery foundation is a cosmetic that is formed by adding oil components, as the binder, to powder components, mixing, and then filling and molding in a container. The powder components thereof are mainly inorganic pigments, organic pigments and resin powder. The pigments are further divided into colored/pearl pigments that adjust color tone and gloss of cosmetics, and other extender pigments. The representative extender pigments are plate-like powder of talc, mica, kaolin, etc. Such components are the majority of powder components and strongly influence the moldability, adhesion, texture, etc. of cosmetics. The characteristics of powder cosmetics largely depend on characteristic extender pigments such as boron nitride, synthetic fluorphlogopite, and barium sulfate in addition to such basic extender pigments.

Among them, boron nitride has a lubricating property and imparts a suitable concealing ability and comfortable adhesion to cosmetics; and is thus a component that is desired to be blended in a large amount.

The conventional titanium dioxide is high in concealing ability for pigmented spots of skin, whereas when it is blended in a large amount to enhance concealing ability, the makeup finish may become unnatural and unevenness of skin may become more noticeable.

From such circumstances, development in a powder cosmetic, including boron nitride and other layered plate-type silicates, that is excellent in texture and a uniform makeup finish, and further provides a natural makeup finish upon application to skin, is being desired.

CITATION LIST

Patent Literatures

PATENT LITERATURE 1: Japanese Unexamined Patent Publication No. 2000-191325 A
PATENT LITERATURE 2: Japanese Unexamined Patent Publication No. 2010-24189 A
PATENT LITERATURE 3: Japanese Unexamined Patent Publication No. 2006-265134 A
PATENT LITERATURE 4: Japanese Unexamined Patent Publication No. 2010-173863 A

DISCLOSURE OF THE INVENTION

Problem to be Solved by the Invention

The present invention has been made in view of the above-mentioned conventional art, and an object to be solved is to provide a powder cosmetic that is excellent in texture and a uniform makeup finish and provides natural makeup finish upon application to skin. by blending boron nitride and other layered plate silicates.

Means to Solve the Problem

The present inventors have diligently investigated on the above-mentioned problem, and as a result, it is found that titanium dioxide obtained by calcining a specific titanium dioxide to have a specific particle size, a specific crystallite size and a specific surface area shows an excellent red-light selective transmission function while having a sufficient concealing ability required for cosmetics. Additionally, it is found that the above-mentioned titanium dioxide blended with boron nitride and a layered plate silicate is excellent in texture, provides natural makeup finish but unnatural whiteness upon application to skin.

That is, a titanium dioxide powder according to the present invention has an apparent average particle size of 100 nm or more and less than 500 nm; an average crystallite size, measured by X-ray diffractometry, of 15 to 30 nm; a specific surface area of 10 to 30 m$^2$/g; is a particle having a shape in which needle-shaped projections that projects out radially are coagulated, and a ratio between a minor axis and a major axis (major axis/minor axis) of 1.0 or more and less than 2.5.

In the titanium dioxide powder, the ratio between the minor axis and the major axis (major axis/minor axis) is preferably 1.0 to 2.0.

A powder cosmetic according to the present invention comprises:

0.1 to 30% by mass of a titanium dioxide powder that has an apparent average particle size of 100 nm or more and less than 500 nm, an average crystallite size of 15 to 30 nm, which is measured by X-ray diffractometry; and a specific surface area of 10 to 30 m$^2$/g; and is a particle having a shape in which needle-shaped projections that projects out radially are coagulated;

1 to 20% by mass of boron nitride; and
10 to 50% by mass of a layered plate silicate.

A solid powder cosmetic according to the present invention comprises:

1 to 30% by mass of a rutile having an average crystallite size of 15 to 30 nm, which is measured by X-ray diffractometry, a specific surface area of 10 to 30 m$^2$/g, a 1.3 times larger reflectance at 450 nm than a reflectance at 650 nm, and a color difference (ΔE) of 22 or less;

1 to 20% by mass of boron nitride; and
10 to 50% by mass of a layered plate silicate.

With respect to the color difference (ΔE), the titanium dioxide powder was dispersed and mixed to a nitrocellulose lacquer in a concentration of 5%, and the obtained dispersion was applied to a black-and-white concealing ability test chart, JIS-K5400, at a coating thickness of 0.101 μm and dried to prepare a test sample. Using the prepared test sample, a colorimetric measurement was performed on each coating surface of a black portion and a white portion of the chart with a spectrocolorimeter. The color difference (ΔE) was calculated based on Hunter Lab color space.

A powder cosmetic according to the present invention comprises:

1 to 30% by mass of a titanium dioxide powder which is a rutile titanium dioxide powder obtained by calcining a rutile titanium dioxide having needle-shaped projections on the particle surface where needle-shaped particles are radially orientated and aggregated and satisfying the following (a) to (c), the titanium dioxide powder having an apparent average particle size of 100 nm or more and less than 500 nm, an average crystallite size measured by X-ray diffractometry is 15 to 30 nm, and a specific surface area of 10 to 30 m$^2$/g;

1 to 20% by mass of boron nitride; and
10 to 50% by mass of a layered plate silicate.
(a) An apparent average particle size is 100 nm or more and less than 500 nm
(b) An average crystallite size measured by X-ray diffractometry is 1 to 25 nm
(c) A specific surface area is 40 to 200 m$^2$/g A powder cosmetic according to the present invention comprises:

1 to 30% by mass of a titanium dioxide powder which is a rutile titanium dioxide powder obtained by calcining a rutile titanium dioxide having needle-shaped projections on the particle surface and satisfying the following (a) to (c), the titanium dioxide powder in which a specific surface area of the rutile titanium dioxide powder after the calcination is 8 to 50% with respect to that of before the calcination;

1 to 20% by mass of boron nitride; and
10 to 50% by mass of a layered plate silicate.
(a) An apparent average particle size is 100 nm or more and less than 500 nm
(b) An average crystallite size measured by X-ray diffractometry is 1 to 25 nm
(c) A specific surface area is 40 to 200 m$^2$/g In the powder cosmetic, the calcination temperature of the titanium dioxide is preferably 500 to 800° C.

In the powder cosmetic, the calcination temperature of the titanium dioxide is preferably 550 to 750° C.

In the powder cosmetic, the aspect ratio between the layered plate silicates is preferably 30 to 80.

In the powder cosmetic, the average particle size of the layered plate silicate is preferably 2 to 20 μm.

Effect of the Invention

According to the present invention, a powder cosmetic which is excellent in makeup finish and texture and has an excellent function of transmitting more light in a long wavelength region (red light selective transmission function) while concealing ability is maintained can be provided.

MODE FOR CARRYING OUT THE INVENTION

Figure 1:
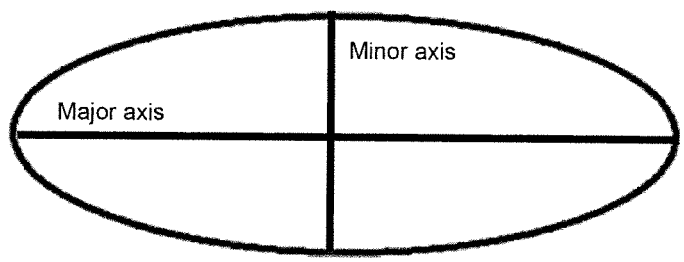
FIG. 1 shows a method for measuring an apparent average particle size.

The titanium dioxide powder according to the present invention is a titanium dioxide powder obtained by calcining titanium dioxide having needle-shaped projections on the particle surface where needle-shaped particles are radially orientated and aggregated at 500 to 800° C., and more preferably at 550 to 750° C. The titanium dioxide powder has an average crystallite size measured by X-ray diffractometry of 15 to 30 nm; an apparent average particle size of titanium dioxide of 100 nm or greater and less than 500 nm, and more preferably 200 to 400 nm; and a specific surface area of 10 to 30 m$^2$/g.

[Titanium Dioxide used as a Mother Nucleus]

The crystalline forms of titanium dioxide used as a mother nucleus include anatase and rutile by crystal structure. The crystalline form of titanium dioxide used in the present invention needs to be rutile which has a high concealing ability since it is low in photocatalytic activity and high in refractive index.

As a rutile titanium dioxide used as a mother nucleus, the titanium dioxide having a function of transmitting red light is used. Considering that a shrinkage phenomenon usually takes place after the calcination, an apparent average particle size of the titanium dioxide used as a mother nucleus is desired to be 100 nm or more and less than 500 nm, and more preferably 200 to 400 nm in terms of achieving the concealing ability by light scattering and the excellent function of transmitting red light of the titanium dioxide obtained in the present invention.

The rutile titanium dioxide used as a mother nucleus may be in a shape of cocoon, straw bundle, strip, sphere, needle, rod or the like. In the present invention, it is preferable to have needle-shaped projections on the particle surface where rod-shaped or needle-shaped particles are radially orientated and aggregated.

The specific surface area of the titanium dioxide used as a mother nucleus is preferably 40 to 200 m$^2$/g in terms of improving an apparent refractive index efficiently by calcination.

The rutile titanium dioxide used as a mother nucleus preferably has an average crystalline size measured by X-ray diffractometry of 1 to 25 nm.

The rutile titanium dioxide used as a mother nucleus may be commercially available products. Examples thereof include ST-700 series manufactured by Titan Kogyo, Ltd. Among the ST-700 series, ST-710 may be used.

[Titanium Dioxide Powder used in the Present Invention]

The titanium dioxide powder of the present invention can be obtained by calcining titanium dioxide used as a mother nucleus.

A calcination temperature depends on a device that performs calcination. However, it is desired that a temperature condition is set so that: voids which are present between the needle-shaped particles, in which needle-shaped projections that exist before the calcination and radially project out from the particle surface, due to coagulation by calcination are reduced; and an average crystallite size measured by X-ray diffractometry is not increased excessively due to sintering of the needle-shaped particles. Such a temperature condition allows both the concealing ability and the red-light selective transmission function to be achieved sufficiently.

The titanium dioxide powder used in the present invention is in form of particles in which needle-shaped projections that exist before the calcination and radially project out from the particle surface are coagulated by calcining. A ratio between a minor axis and a major axis of the particle (major axis/minor axis) is 1.0 or more and less than 2.5, and more preferably 1.0 to 2.0.

A suitable calcination temperature varies depending on the calcination device. When calcination is performed in a muffle furnace or a rotary kiln which is a commonly-used calcination furnace, it is desired that calcination is performed at a temperature of 500 to 800° C., and more preferably at 550 to 750° C. When the temperature is below 500° C., the concealing ability is insufficient since voids that exist before the calcination are not sufficiently reduced. When the temperature exceeds 800° C., the red-light selective transmission function is lost since the sintering proceeds excessively.

The titanium dioxide of the present invention needs to have the average crystallite size measured by X-ray diffractometry of 15 to 30 nm.

When the crystallite size is less than 15 nm, it is not preferable because the sufficient concealing ability cannot be obtained. Additionally, when the crystallite size is more than 30 nm, it is not preferable because the sufficient red-light selective transmission function is lost as the sintering proceeds.

Further, the titanium dioxide powder of the present invention needs to have the apparent average particle size of 100 nm or more and less than 500 nm, and more preferably 200 to 400 nm, in terms of efficiently achieving the concealing ability due to light scattering and excellence in the red-light transmission function.

The specific surface area of the titanium dioxide powder used in the present invention is an index that shows a reduction in voidage and a progression of the sintering of the obtained titanium dioxide particles. The specific surface area after the calcination of the titanium dioxide powder used as a mother nucleus is preferably within a range of 8 to 50%, and more preferably 8 to 30% compared to before the calcination (100%).

Furthermore, the specific surface area of the titanium dioxide powder of the present invention needs to be 10 to 30 m$^2$/g. The specific surface area of less than 10 m$^2$/g is not preferable because the sintering proceeds and thus the sufficient red-light selective transmission function is lost. Additionally, the specific surface area of more than 30 m$^2$/g is not preferable because the sufficient concealing ability cannot be achieved due to the existence of too many voids.

The titanium dioxide powder of the present invention can be surface treated after the calcination. Performing surface treatment can improve long-lasting makeup properties involving viscosity, dispersibility to oil, and water repellency, and at the same time, produce a titanium dioxide that is excellent in texture.

Examples of inorganic substances which can be used as a surface treatment agent include a hydrous oxide or oxide of metals such as aluminum, silicon, zinc, titanium, zirconium, iron, cerium, and tin. The metallic salt to be used is not limited in particular.

Examples of an organic substance, which can be used as a surface treatment agent after surface treatment with metal oxide or hydroxide such as aluminum hydroxide or oxide and is intended to impart a lipophilic property, include fatty acids such as stearic acid, oleic acid, isostearic acid, myristic acid, palmitic acid, and behenic acid, silicone compounds such as methylhydrogenpolysiloxane, dimethicone, alkyl (C8-C18 or the like)trialkoxysilane, amino-modified silicone, and carboxyl-modified silicone, fluorine compounds such as perfluoroalkyl alkyl phosphate, dextrin myristate, dextrin palmitate, and amino acid derivatives such as lauroyl lysine, lauroyl glutaminate, or the like.

It is preferable that these surface treatment agents are 1 to 10% by mass with respect to the titanium dioxide powder since the concealing ability is high.

The titanium dioxide powder used in the present invention can be widely blended in cosmetics, pigments, inks, and paints.

The blending amount of titanium dioxide used in the present invention is 1 to 30% by mass, and more preferably 5 to 15% by mass with respect to the total weight of the powder cosmetic. When the blending amount is less than 1% by mass, the effect achieved by the blending of titanium dioxide of the present invention may not be achieved. When the blending amount exceeds 30% by mass, the makeup finish may be unnatural.

[Boron Nitride]

Boron nitride used in the present invention is not limited in particular as long as it is generally used in cosmetics. Commercially available products such as RonaFlair® Boroneige SF-12 (manufactured by Merck KGaA), SHP-3 and SHP-6 (both manufactured by Mizushima Ferroalloy Co., Ltd.), or the like may be used. In order to improve dispersibility or adhesiveness, those that are surface-treated with silicones, fluorine compounds, metal soaps, or oil agents may be used.

The blending amount of boron nitride used in the present invention is 1 to 20% by mass, and more preferably 3 to 15% by mass with respect to the total weight of the powder cosmetic. When it is less than 1% by mass, the effect achieved by the blending of boron nitride may not be achieved. When the blending amount exceeds 20% by mass, the makeup finish may be poor.

[Layered Plate Silicate]

In the present invention, layered plate silicates such as synthetic fluorine phlogopite iron, mica, synthetic fluorine phlogopite, sericite, or the like are used preferably.

Synthetic fluorine phlogopite iron and synthetic fluorine phlogopite used in the present invention are not limited in particular as long as they are generally used in cosmetics. Those having an average particle of 2 to 20 μm, and more preferably 5 to 15 μm are preferable. PDM-FE (manufactured by Topy Industries, Ltd.) may be an example of such synthetic fluorine phlogopite iron. PDM-5L, 10L (manufactured by Topy Industries, Ltd.) may be examples of such synthetic fluorine phlogopite. In order to improve dispersibility or adhesiveness, those that are surface-treated with silicones, fluorine compounds, metal soaps, or oil agents may be used.

The blending amount of the layered plate silicate used in the present invention is 10 to 50% by mass, and more preferably 20 to 45% by mass with respect to the total amount of the cosmetic. When it is less than 10% by mass, the makeup finish of the cosmetic may deteriorate. When the blending amount exceeds 50% by mass, uniformity of the makeup finish may be poor.

It is more preferable when the aspect ratio between the layered plate silicate used in the present invention is within a range of 30 to 80.

[Other Components]

The powder cosmetic according to the present invention may include, as appropriate and as necessary, other components within the range of not inhibiting the effect of the present invention such as esters, anionic surfactants, cationic surfactants, amphoteric surfactants, nonionic surfactants, moisturizers, water-soluble polymers, thickeners, film-forming agents, ultraviolet light absorbers, sequestrants, lower alcohols, polyhydric alcohols, saccharides, amino acids, organic amines, polymer emulsions, pH adjusters, skin nutrients, vitamins, antioxidants, anti-oxidant aids, perfumes, water and the like, and can be produced by a usual method in accordance with the aimed dosage forms.

Specific components that can be blended are listed below. The powder cosmetic can be prepared by blending the above-mentioned essential components and one or two or more of the optional components below.

Examples of anionic surfactants include, but not limited to: fatty acid soap (such as sodium laurate and sodium palmitate); higher alkyl sulfate ester salt (such as sodium lauryl sulfate and potassium lauryl sulfate); alkyl ether sulfate ester salt (such as POE-lauryl sulfate triethanolamine and sodium POE-lauryl sulfate); N-acyl sarcosinic acid (such as sodium lauroyl sarcosinate); higher fatty acid amide sulfonate (such as sodium N-myristoyl-N-methyltaurate, sodium methyl cocoyl taurate and sodium laurylmethyl taurate); phosphate ester salt (sodium POE-oleylether phosphate and POE-stearylether phosphate); sulfosuccinate (such as sodium di-2-ethylhexyl sulfosuccinate, sodium monolauroyl monoethanolamide polyethylene sulfosuccinate and sodium lauryl polypropylene glycol sulfosuccinate); alkylbenzene sulfonate (such as sodium linear dodecylbenzene sulfonate, triethanolamine linear dodeylbenzene sulfonate, and linear dodecylbenzene sulfonate); higher fatty acid ester sulfate ester salt (such as sodium hydrogenated gryceryl cocoate sulfate); N-acyl glutamate (such as monosodium N-lauroyl glutamate, disodium N-stearoyl glutamate and monosodium N-myristoyl-L-glutamate); sulfonated oil (such as Turkey red oil); POE-alkyl ether carboxylic acid; POE-alkyl aryl ether carboxylate; α-olefin sulfonate; higher fatty acid ester sulfonate; secondary alcohol sulfate ester salt; higher fatty acid alkylolamide sulfate ester salt; sodium lauroyl monoethanolamide succinate; N-palmitoyl asparaginate ditriethanolamine; and sodium casein.

Examples of cationic surfactants include, but not limited to: alkyltrimethyl ammonium salt (such as stearyltrimethyl ammonium chloride, lauryltrimethyl ammonium chloride); alkylpyridinium salt (such as cetylpyridinium chloride); distearyldimethyl ammonium chloride; dialkyldimethyl ammonium salt; poly (N,N'-dimethyl-3,5-methylenepiperidinium) chloride; alkyl quaternary ammonium salt; alkyldimethylbenzyl ammonium salt; alkylisoquinolinium salt; dialkylmorphonium salt; POE alkylamine; alkylamine salt; polyamine fatty acid derivative; amyl alcohol fatty acid derivative; benzalkonium chloride; and benzethonium chloride.

Examples of amphoteric surfactants include, but not limited to: imidazoline-based amphoteric surfactant (such as sodium 2-undecyl-N,N,N-(hydroxyethylcarboxymethyl)-2-imidazoline and 2-cocoyl-2-imidazolinium hydroxide-1-carboxyethyloxy disodium salt); and betaine-based surfactant (such as 2-heptadecyl-N-carboxymethyl-N-hydroxyethyl imidazolinium betaine, lauryl dimethylaminoacetic acid betaine, alkyl betaine, amidobetaine, and sulfobetaine).

Examples of lipophilic nonionic surfactants include, but not limited to: sorbitan fatty acid ester (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, diglycerol sorbitan tetra-2 ethylhexylate, etc.); glyceryl polyglyceryl fatty acid (such as glyceryl monocotton oil fatty acid, glyceryl monoerucate, glyceryl sesquioleate, glyceryl monostearate, glyceryl α, α'-oleate pyroglutamate, glyceryl monostearate malate, etc.); propylene glycol fatty acid ester (such as propylene glycol monostearate, etc.); hydrogenated castor oil derivative; and glyceryl alkyl ether.

Examples of hydrophilic nonionic surfactants include, but not limited to: POE sorbitan fatty acid ester (such as POE sorbitan monooleate, POE sorbitan monostearate, POE sorbitan monooleate, POE sorbitan tetraoleate); POE sorbit fatty acid ester (such as POE sorbit monolaurate, POE sorbit monooleate, POE sorbit pentaoleate, POE sorbit monostearate), POE glyceryl fatty acid ester (such as POE monooleate such as POE glyceryl monostearate, POE glyceryl monoisostearate, POE glyceryl triisostearate); POE fatty acid ester (such as POE distearate, POE monodioleate, ethyleneglycol distearate); POE alkyl ether (such as POE lauryl ether, POE oleyl ether, POE stearyl ether, POE behenyl ether, POE-2-octyldodecyl ether, POE cholestanol ether); puluronic type (such as Puluronic), POE/POP alkyl ethers (such as POE/POP cetyl ether, POE/POP 2-decyltetradecyl ether, POE/POP monobutyl ether, POE/POP hydrogenated lanoline, POE/POP glycerin ether); tetra POE/tetra POP ethylenediamine condensation products (such as Tetronic); POE castor oil hydrogenated castor oil derivative (such as POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated oil maleate); POE beeswax/lanoline derivative (such as POE sorbitol beeswax); alkanolamide (such as coconut oil fatty acid diethanolamide, lauric acid monoethanolamide, fatty acid isopropanolamide); POE propyleneglycol fatty acid ester; POE alkyl amines; POE fatty acid amide; sucrose fatty acid ester; alkylethoxydimethylamine oxide; and trioleyl phosphoric.

Examples of moisturizers include, but not limited to, polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salt, dl-pyrrolidone carboxylate, alkyleneoxide derivative, short-chain soluble collagen, diglycerin (EO)PO adduct, chestnut rose extract, yarrow extract, and melilot extract.

Examples of natural water-soluble polymers include, but not limited to: plant based polymer (such as gum Arabic, gum tragacanth, galactan, guar gum, locust bean gum, gum karaya, carrageenan, pectin, agar, quince seed (cydonia oblonga), algae colloid (brown algae extract), starch (rice, corn, potato, wheat), glicyrrhizic acid); microorganism based polymer (such as xanthan gum, dextran, succinoglycan, pullulan, etc.), and animal based polymer (such as collagen, casein, albumin, gelatin, etc.).

Examples of semisynthetic water-soluble polymers include, but not limited to: starch based polymer (such as carboxymethyl starch, methylhydroxypropyl starch, etc.); cellulose based polymer (such as methylcellulose, ethylcellulose, methylhydroxypropylcellulose, hydroxyethylcellulose, cellulose sodium sulfate, hydroxypropylcellulose, carboxymethylcellulose, sodium carboxymethyl cellulose, crystalline cellulose, cellulose powder, etc.); and algin acid-based polymer (such as sodium alginate, propylene glycol alginate ester, etc.).

Examples of synthetic water-soluble polymers include, but not limited to: vinyl based polymer (such as polyvinyl alcohol, polyvinyl methyl ether, polyvinylpyrrolidone, carboxyvinylpolymer, etc.); polyoxyethylene based polymer (such as polyoxyethylenepolyoxypropylene copolymer such as polyethylene glycol 20,000, 40,000 and 60,000, etc.); acrylic polymer (such as sodium polyacrylate, polyethylacrylate, polyacrylamide, etc.); polyethyleneimine; and cationic polymer.

Examples of thickeners include, but not limited to, gum arabic, carrageenan, karaya gum, tragacanth gum, carob gum, quince seed (marmelo), casein, dextrin, gelatin, sodium pectate, sodium alginate, methylcellulose, ethyl cellulose, CMC, hydroxyethyl cellulose, hydroxypropyl cellulose, PVA, PVM, PVP, sodium polyacrylate, carboxyvinyl polymer, locustbean gum, guar gum, tamarind gum, dialkyldimethylammonium sulfate cellulose, xanthan gum, magnesium aluminum silicate, bentonite, hectorite, magnesium aluminum silicate (veegum), laponite, and silicic anhydride.

Examples of ultraviolet light absorbers include, but not limited to: benzoic acid family ultraviolet light absorbers (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc.); anthranilic acid family ultraviolet light absorbers (such as homomenthyl N-acetylanthranilate etc.); salicylic acid family ultraviolet light absorbers (such as amyl salicylate, menthyl salicylate, homomenthyl salicylate, octyl salicylate, phenyl salicylate, benzyl salicylate, p-isopropanolphenyl salicylate, etc.); cinnamic acid family ultraviolet light absorbers (such as octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, etc.); benzophenone family ultraviolet light absorbers (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc.); 3-(4'-methylbenzylidene)-d,l-camphor and 3-benzylidene-d,l-camphor; 2-phenyl-5-methylbenzoxazol; 2,2'-hydroxy-5-methylphenylbenzotriazol, 2-(2'-hydroxy-5'-t-octylphenyl)benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; dimorpholinopyridazinone; 2-ethylhexyl 2-cyano-3,3-diphenylacrylate; and 2,4-bis-{[4-(2-ethylhexyloxy)-2-hydroxy]-phenyl}-6-(4-methoxyphenyl)-(1,3,5)-triazine.

Examples of sequestrants include, but not limited to, 1-hydroxyethane-1, 1-diphosphonic acid, 1-hydroxyethane, 1-diphosphonic acid 4 Na salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of lower alcohols include, but not limited to, ethanol, propanol, isopropanol, isobutyl alcohol, and t-butyl alcohol.

Examples of polyhydric alcohols include, but not limited to: dihydric alcohol (such as ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc.); trihydric alcohol (such as glycerin, trimethylolpropane, etc.); tetrahydric alcohol (such as such as pentaerythritol such as 1,2,6-hexanetriol, etc.); pentahydric alcohol (such as xylitol, etc.); hexahydric alcohol (such as sorbitol, mannitol, etc.); polyhydric alcohol polymer (such as diethylene glycol, dipropylene glycol, triethylene glycol, polypropylene glycol, tetraethylene glycol, diglycerin, polyethylene glycol, triglycerin, tetraglycerin, polyglycerin, etc.); dihydric alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, etc.); dihydric alcohol alkyl ethers (such as diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc.); dihydric alcohol ether ethers (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc.); glycerin monoalkyl ether (such as chimyl alcohol, selachyl alcohol, batyl alcohol, etc.); sugar alcohol (such as sorbitol, maltitol, maltotriose, mannitol, sucrose, erythritol, glucose, fructose, starch sugar, maltose, xylitose, starch sugar hydrogenated alcohol, etc.); glycolide, tetrahydrofurfuryl alcohol; POE-tetrahydrofurfuryl alcohol; POP/POE-butyl ether; tripolyoxypropylene glycerin ether; POP-glycerin ether; POP-glycerin ether phosphoric acid; POP/POE-pentaerythritol ether; and polyglycerin.

Examples of monosaccharides include, but not limited to: triose (such as D-glyceryl aldehyde, dihydroxyacetone, etc.); tetrose (such as D-erythrose, D-erythrulose, D-threose, erythritol, etc.); pentaose (such as L-arabinose, D-xylose, L-lyxose, D-arabinose, D-ribose, D-ribulose, D-xylulose, L-xylulose, etc.); hexalose (such as D-glucose, D-talose, D-psicose, D-galactose, D-fructose, L-galactose, L-mannose, D-tagatose, etc.); heptose (such as aldoheptose, heplose); octose (such as octulose, etc.); deoxy sugar (such as 2-deoxy-D-ribose, 6-deoxy-L-galactose, 6-deoxy-L-mannose, etc.); amino sugar (such as D-glucosamine, D-galactosamine, sialic acid, amino uronic acid, muramic acid, etc.); and uronic acid (such as D-grucuronic acid, D-mannuronic acid, L-guluronic acid, D-garacturonic acid, L-iduronic acid, etc.).

Examples of oligosaccharides include, but not limited to, sucrose, guntianose, umbelliferose, lactose, planteose, isolignoses, α,α-trehalose, raffinose, lignoses, umbilicin, stachyose, and verbascoses.

Examples of polysaccharides include, but not limited to, cellulose, quince seed, chondroitinsulfate, starch, galactan, dermatan sulfate, glycogen, gum Arabic, heparansulfate, hyaluronan, gum tragacanth, keratan sulfate, chondoroitin, xanthan gum, mucoitin sulfate, guar gum, dextran, keratosulfate, locust bean gum, succinoglycan, and caronic acid.

Examples of amino acids include, but not limited to: neutral amino acid (such as threonine, cysteine, etc.); and basic amino acid (such as hydroxylysine, etc.). Examples of amino acid derivatives include, but not limited to, sodium acyl sarcosinate (sodium lauroyl sarcosinate), acyl glutamate, sodium acyl β-alanine, glutathione, and pyrrolidone carboxylate.

Examples of organic amines include, but not limited to, monoethanolamine, diethanolamine, triethanolamine, morpholine, triisopropanolamine, 2-amino-2-methyl-1,3-propanediol, and 2-amino-2-methyl-1-propanol.

Examples of polymer emulsions include, but not limited to, acrylic resin emulsion, ethyl polyacrylate emulsion, acrylic resin solution, polyacrylalkylester emulsion, polyvinyl acetate resin emulsion, and natural rubber latex.

Examples of pH adjusters include, but not limited to, buffers such as lactic acid-sodium lactate, citric acid-sodium citrate, and succinic acid-sodium succinate.

Examples of vitamins include, but not limited to, vitamine A, B1, B2, B6, C, E and derivatives thereof, pantothenic acid and derivatives thereof, and biotin, Examples of anti-oxidants include, but not limited to, tocopherols, dibutyl hydroxy toluene, butyl hydroxy anisole, and gallic acid esters Examples of anti-oxidant aids include, but not limited to, phosphoric acid, citric acid, ascorbic acid, maleic acid, malonic acid, succinic acid, fumaric acid, cephalin, hexamethaphosphate, phytic acid, and ethylenediaminetetraacetic acid.

Examples of other blendable compositions include, but not limited to: antiseptic agents (such as ethylparaben, butylparaben, chlorphenesin, 2-phenoxyethanol, etc.); antiphlogistics (such as glycyrrhizinic acid derivatives, glycyrrhetic acid derivatives, salicylic acid derivatives, hinokitiol, zinc oxide, allantoin, etc.); skin-whitening agents (such as placental extract, saxifrage extract, arbutin, etc.); various extracts (such as phellodendron bark (cork tree bark), coptis rhizome, lithospermum, peony, swertia herb, birch, sage, loquat, carrot, aloe, mallow, iris, grape, coix seed, sponge gourd, lily, saffron, cnidium rhizome, ginger, hypericum, restharrow, garlic, red pepper, citrus unshiu, Japanese angelica, seaweed, etc.); activators (such as royal jelly, photosenstizer, cholesterol derivatives, etc.); blood circulation promotors (such as nonylic acid vanillylamide, nicotine acid benzyl ester, nicotine acid β-butoxyethyl ester, capsaicin, zingerone, cantharides tincture, ichthammol, tannic acid, α-borneol, tocopheryl nicotinate, meso-inositol hexanicotinate, cyclandelate, cinnarizine, tolazoline, acetylcholine, verapamil, cepharanthine, γ-oryzanol, etc.); antiseborrheric agents, (such as sulfur, thianthl, etc.); and anti-inflammatory agents (such as tranexamic acid, thiotaurine, hypotaurine, etc.).

Furthermore, sequestrants such as disodium edetate, trisodium edetate, sodium citrate, sodium polyphosphate, sodium metaphosphate, gluconic acid, malic acid, and the like; various crude drug extracts such as cafein, tannin, verapamil, tranexamic acid and derivatives thereof, licorice, Chinese quince, Pyrola japonica and the like; drugs such as tocopherol acetate, glycyrrhetinic acid, glycyrrhizic acid and derivatives thereof, or salts thereof; skin-whitening agents such as vitamin C, magnesium ascorbyl phosphate, ascorbic acid glucoside, arbutin, kojic acid and the like; amino acids such as arginine and lysine and the like and derivatives thereof; and saccharides such as fructose, mannose, erythritol, trehalose, xylitol, and the like can also be blended.

The product forms of the powder cosmetic according to the present invention can be in any product forms that fall within the category of powder cosmetics. Examples of specific product forms include, but not limited to, foundations, eye shadows, blushes, body powders, perfume powders, baby powders, pressed powders, deodorant powders, and face powders.

[Production Method of the Solid Powder Cosmetic]
<Dry Production Method>

An inorganic powder component, an oily component, and other components were mixed by a Henschel mixer to be crushed by a pulverizer for two times. Then, the obtained mixture was filled in an inner plate type container made of resin and subjected to a dry press molding by a well-known method to give a solid powder cosmetic blended with titanium dioxide of the present invention.

<Other Production Methods>

Well-known methods can be used as the production method of blending titanium dioxide of the present invention to the cosmetic. For example, the production method of preparing the cosmetic by drying a slurry that uses a volatile solvent described in Japanese Patent No. 5422092, or the production method of preparing the cosmetic by removing a slurry that uses a volatile solvent after filling described in Japanese Patent No. 5972437 can be used preferably.

EXAMPLES

The present invention will be described with reference to the following examples. However, the present invention is not limited to the following examples. The unit of the blending amount is "% by mass" with respect to the system to which the component is to be blended unless otherwise specified.

Before describing Examples, evaluation method of the test of titanium dioxide used in the present invention is described.

Evaluation (1): Method for Measuring Average Crystallite Size

A sample was measured by an X-ray diffractometry (Geigerflex, manufactured by Rigaku Corporation). The average crystallite size was calculated by Scherrer's equation.

Evaluation (2): Evaluation of Concealing Ability

A titanium dioxide powder was dispersed and mixed into a nitrocellulose lacquer in a concentration of 5%. A resultant dispersion was applied to a black-and-white concealing ability test chart in accordance with JIS-K5400 with a coating thickness of 0.101 μm and dried to prepare a test sample. Using the prepared test sample, a colorimetric measurement was performed on each coating surface of a black portion and a white portion of the chart with a spectrocolorimeter (CM-2600, manufactured by Konica Minolta, Inc.). A color difference (ΔE) was calculated based on Hunter Lab color space and evaluated it as the concealing ability. Note that the higher the ΔE, the lower the concealing ability; and the lower the ΔE, the higher the concealing ability.

$$\Delta E=\sqrt{(L1-L2)^2+(a1-a2)^2+(b1-b2)^2}$$

(Evaluation Criteria)
A: ΔE≤22
B: 22<ΔE≤25
C: 25<ΔE

Evaluation (3): Evaluation of Red-Color Transmitting Property

Among spectral reflectances at each wavelengths measured on the black portion of the chart, similar to the concealing ability described above, the reflectances at wavelengths of 450 nm and 650 nm were used to calculate their ratio, (reflectance at a wavelength of 450 nm/reflectance at 650 nm: R450/R650). The ratio represents a red-color transmitting property.

Note that the higher the R450/R650, the higher the red-color transmitting property; and the lower R450/R650, the lower the red-color transmitting property.

(Evaluation Criteria)
A: 1.4<R450/R650
B: 1.35<R450/R650≤1.4
C: 1.3<R450/R650≤1.35
D: R450/R650≤1.3

Evaluation (4): Method for Measuring Specific Surface Area

The specific surface area per unit mass can be determined by a nitrogen adsorption method known as the BET (Brunauer-Emmett-Teller) method described in The Journal of the American Chemical Society, vol. 60, p. 309, February 1938 which corresponds to the ISO international standard 5794-1 (Appendix D)

Evaluation (5): Method for Measuring Apparent Average Particle Size

The method shown in FIG. 1 is used to calculate an average value of the lengths of the major axis and the minor axis of the particle.

[Selection of Titanium Dioxide used as a Mother Nucleus]

First of all, the present inventors used commercially available pigment grade rutile and anatase titanium oxides and evaluated them by the above evaluation methods. The results are shown in Table 1.

TABLE 1

| | Test Example | |
|---|---|---|
| | 1<br>Pigment grade<br>titanium<br>dioxide (rutile) *1 | 2<br>Pigment grade<br>titanium<br>dioxide (anatase) *2 |
| Concealing ability (ΔE (Hunter)) | 16.1 | 21.4 |
| Concealing ability evaluation | A | A |
| R450/R650 | 1.18 | 1.14 |
| Red-color transmitting property | D | D |
| Specific surface area m²/g | 5 | 6 |

*1: Tipaque CR-50 (manufactured by ISHIHARA SANGYO KAISHA, LTD., apparent average particle size: 200 nm, form: indefinite form)
*2: Bayer titanium A (manufactured by Bayer AG, apparent average particle size: 400 nm, form: indefinite form)

Both the rutile pigment grade titanium dioxide and the anatase pigment grade titanium dioxide were low in the red-color transmitting property. Even when these titanium oxides were calcined at high-temperature, the red-color transmitting properties were low.

The present inventors investigated on the possibility of producing a titanium dioxide excellent in concealing ability by using a rutile titanium dioxide having a high red-color transmitting property.

The present inventors used the method described in Patent Literature (Japanese Unexamined Patent Publication No. 2010-173863 A) and synthesized two kinds of titanium dioxide having different particle sizes and having needle-shaped projections on the particle surface where needle-shaped particles are radially oriented and aggregated.

The resultant titanium dioxides were called as Titanium dioxide A (specific surface area: 101 m²/g, crystallite size: 5 nm, apparent average particle size: 0.2 to 0.3 μm, with needle-shaped projections) and Titanium dioxide B (specific surface area: 117 m²/g, crystallite size: 11 nm, apparent average particle size: 0.3 μm, with needle-shaped projections), respectively.

Titanium dioxide having needle-shaped projections on the particle surface where needle-shaped particles are radially orientated and aggregated which was commercially available (ST-730, manufactured by Titan Kogyo, Ltd.) was called as Titanium dioxide C (specific surface area: 98 m²/g, crystallite size: 6 nm, apparent average particle size: 0.5 μm, with needle-shaped projections).

Titanium dioxide having needle-shaped projections on the particle surface where needle-shaped particles are radially orientated and aggregated which was commercially available (ST-750, manufactured by Titan Kogyo, Ltd.) was called as Titanium dioxide D (specific surface area: 84 m²/g, crystallite size: 8.6 nm, apparent average particle size: 1.0 μm, with needle-shaped projections).

Titanium dioxide in which the particles are needle-shaped and which was commercially available (MT062, manufactured by Tayca Corporation) was called as Titanium dioxide E (specific surface area: 47 m²/g, crystallite size: 23.3 nm, apparent average particle size: 65 nm, with needle-shaped projections).

Each titanium dioxide was used to produce a titanium dioxide powder by the following method. The produced titanium dioxide powder was evaluated by the above evaluation methods and was investigated on each relationship between each kind of titanium dioxide before calcination and each calcination temperature. The results are shown in Tables 2 to 6.

(Production Method of Titanium Dioxide Powder)

100 g of titanium dioxide to be used as a mother nucleus was placed in a crucible made of quartz. Then, it was calcined at each temperature for 1 hour in a muffle furnace to produce a titanium dioxide powder.

Titanium dioxide A (specific surface area: 101 m²/g, crystallite size: 5 nm, apparent average particle size: 0.2 to 0.3 μm, with needle-shaped projections)

TABLE 2

| Test example | 1-1 | 1-2 | 1-3 | 1-4 | 1-5 | 1-6 |
|---|---|---|---|---|---|---|
| Calcination temperature | 0 | 300 | 500 | 700 | 800 | 900 |
| Concealing ability (ΔE (Hunter)) | 33.9 | 26.2 | 22.7 | 19.9 | 18.3 | 17.6 |
| Concealing ability evaluation | C | C | B | A | A | A |
| R450/R650 | 1.58 | 1.45 | 1.43 | 1.42 | 1.29 | 1.14 |
| Red-color transmitting property evaluation | A | A | A | A | D | D |
| Ratio between minor axis and major axis | 1.4 | 1.4 | 1.4 | 1.4 | 1.3 | 1.3 |
| Specific surface area m²/g | 101 | 62 | 32 | 14 | 13 | 5 |

Titanium dioxide B (specific surface area: 117 m²/g, crystallite size: 11 nm, apparent average particle size: 0.3 μm, with needle-shaped projections)

TABLE 3

| Test example | 2-1 | 2-2 | 2-3 | 2-4 | 2-5 | 2-6 |
|---|---|---|---|---|---|---|
| Calcination temperature | 0 | 300 | 500 | 700 | 800 | 900 |
| Concealing ability (ΔE (Hunter)) | 34.0 | 25.2 | 21.7 | 18.8 | 16.8 | 17.2 |
| Concealing ability evaluation | C | C | A | A | A | A |
| R450/R650 | 1.57 | 1.48 | 1.42 | 1.40 | 1.31 | 1.19 |
| Red-color transmitting property evaluation | A | A | A | A | C | D |
| Ratio between minor axis and major axis | 1.4 | 1.4 | 1.4 | 1.4 | 1.3 | 1.3 |
| Specific surface area m²/g | 117 | 68 | 30 | 18 | 15 | 6 |

Titanium dioxide C (specific surface area: 98 m²/g, crystallite size: 6 nm, apparent average particle size: 0.5 μm, with needle-shaped projections)

TABLE 4

| Test example | 3-1 | 3-2 | 3-3 | 3-4 | 3-5 | 3-6 |
|---|---|---|---|---|---|---|
| Calcination temperature | 0 | 300 | 500 | 700 | 800 | 900 |
| Concealing ability (ΔE (Hunter)) | 34.8 | 25.9 | 23.2 | 19.6 | 19.3 | 19.1 |
| Concealing ability evaluation | C | C | B | A | A | A |
| R450/R650 | 1.45 | 1.33 | 1.31 | 1.19 | 1.13 | 1.09 |
| Red-color transmitting property evaluation | A | C | C | D | D | D |
| Ratio between minor axis and major axis | 1.3 | 1.3 | 1.3 | 1.3 | 1.3 | 1.3 |
| Specific surface area m²/g | 98 | 56 | 27 | 10 | 9 | 6 |

Titanium dioxide D (specific surface area: 84 m²/g, crystallite size: 8.6 nm, apparent average particle size: 1.0 μm, with needle-shaped projections)

TABLE 5

| Test example | 4-1 | 4-2 | 4-3 | 4-4 |
|---|---|---|---|---|
| Calcination temperature | 0 | 350 | 630 | 720 |
| Concealing ability (ΔE (Hunter)) | 49.5 | 47.6 | 45.2 | 44.6 |
| Concealing ability evaluation | C | C | C | C |
| R450/R650 | 0.9 | 0.9 | 0.9 | 0.9 |
| Red-color transmitting property evaluation | D | D | D | D |
| Ratio between minor axis and major axis | 1.3 | 1.3 | 1.3 | 1.2 |
| Specific surface area m²/g | 84 | 74 | 38 | 34 |

Titanium dioxide E (specific surface area: 47 m²/g, crystallite size: 23.3 nm, apparent average particle size: 65 nm, with needle-shaped projections)

TABLE 6

| Test example | 5-1 | 5-2 | 5-3 | 5-4 |
|---|---|---|---|---|
| Form | needle-shaped | needle-shaped | needle-shaped | needle-shaped |
| Ratio between minor axis and major axis | 3.3 | 3.3 | 3.3 | 3.2 |
| Apparent particle size (nm) | 65 | 65 | 65 | 65 |
| Crystallite size (nm) | 23.3 | 23.3 | 24.3 | 26.9 |
| Specific surface area (m²/g) | 47 | 44 | 40 | 19 |
| Calcination temperature (° C.) | — | 350 | 630 | 720 |
| Red-color transmitting property | A | A | A | A |
| Concealing ability | C | C | C | C |

The concealing ability in Titanium dioxides A to C was improved by increasing the calcination temperature. The specific surface area was decreased as the temperature rose, which tells that the voids existing in the particle were reduced by coagulation of the needle-shaped particles that were radially orientated and aggregated before the calcination. This led to an improvement of the apparent refractive index, and consequently, the concealing ability was improved. However, the red-color transmitting property was gradually deteriorated. In particular, when the calcination was performed at high temperature, sintering was caused excessively, and an initial red-color transmitting property was significantly deteriorated.

In particular, with respect to Titanium dioxide C having a large particle size, the red-color transmitting property was almost lost at 700° C.

With respect to Titanium dioxide D having needle-shaped particles radially orientated and aggregated like Titanium oxides A to C, the specific surface area was decreased as the temperature rose like in Titanium oxides A to C, but an improvement of the concealing ability was extremely small since it has significantly large apparent particle size. Furthermore, the red-color transmitting property was low before and after the calcination since it has significantly large apparent particle size: thus, the desired red-color transmitting property was not achieved.

With respect to Titanium dioxide E having a small article size before the calcination and is formed of a single needle-shaped particle, the shape did not change largely after the calcination and the red-color transmitting property was maintained, but the concealing ability did not improve at all.

Furthermore, titanium dioxide having different shapes were investigated.

Titanium dioxide of which the particles are granular which was commercially available (TTO55(A), manufactured by ISHIHARA SANGYO KAISHA, LTD.) was called as Titanium dioxide F (specific surface area: 37 m²/g, crystallite size: 24.8 nm, apparent average particle size: 50 nm, granular).

Titanium dioxide having rod-shaped particles orientated and aggregated in forms of straw bundles which was commercially available (ST643, manufactured by Titan Kogyo, Ltd.) was called as Titanium dioxide G (specific surface area: 132 m²/g, crystallite size: 8.6 nm, apparent average particle size: 200 nm, in form of straw bundles).

Titanium dioxide F (specific surface area: 37 m²/g, crystallite size: 24.8 nm, apparent average particle size: 50 nm, granular)

TABLE 7

| Test example | 6-1 | 6-2 | 6-3 | 6-4 |
|---|---|---|---|---|
| Form | granular | granular | granular | granular |
| Ratio between minor axis and major axis | 1.7 | 1.7 | 1.7 | 1.7 |
| Apparent particle size | 50 | 50 | 50 | 50 |
| Crystallite size | 24.8 | 25.1 | 24.8 | 26.5 |
| Specific surface area | 37 | 38 | 32 | 35 |
| Calcination temperature | — | 350 | 630 | 720 |
| Red-color transmitting property | A | A | A | A |
| Concealing ability | C | C | C | C |

From Test Examples 6-1 to 6-4, it was found that when granular titanium dioxide is calcined at 350 to 720° C., the crystallite size does not change, and the specific surface area and the crystallite size do not become those of the calcined titanium dioxide of the present invention.

Accordingly, although the red-color transmitting property was achieved, the desired concealing ability was not achieved.

Titanium dioxide G (specific surface area: 132 m²/g, crystallite size: 8.6 nm, apparent average particle size: 200 nm, in form of straw bundles)

TABLE 8

| Test example | 7-1 | 7-2 | 7-3 | 7-4 |
|---|---|---|---|---|
| Form | straw bundles | straw bundles | straw bundles | straw bundles |
| Ratio between minor axis and major axis | 2.5 | 2.5 | 2.5 | 2.5 |
| Apparent particle size | 200 | 200 | 200 | 200 |
| Crystallite size | 8.6 | 8.7 | 9.9 | 11.1 |
| Specific surface area | 132 | 79 | 34 | 39 |
| Calcination temperature | — | 350 | 630 | 720 |
| Red-color transmitting property | C | C | C | C |
| Concealing ability | C | B | B | B |

Like the titanium dioxide used as a mother nucleus in the present invention, the titanium dioxide used in Test Example 7-1 satisfies: (a) the apparent average particle size; (b) the average crystallite size measured by X-ray diffractometry; and (c) the specific surface area, but does not have needle-shaped projections on the particle surface. Moreover, sufficient red-color transmitting property and concealing ability cannot be achieved after the calcination since the ratio between the minor axis and the major axis is as large as 2.5.

From the above consideration, Titanium dioxide B having an acceptable temperature width in terms of improvement in the concealing ability and maintaining of the red-color transmitting property is suitable as titanium dioxide used as a mother nucleus in the present invention.

Figure 2:
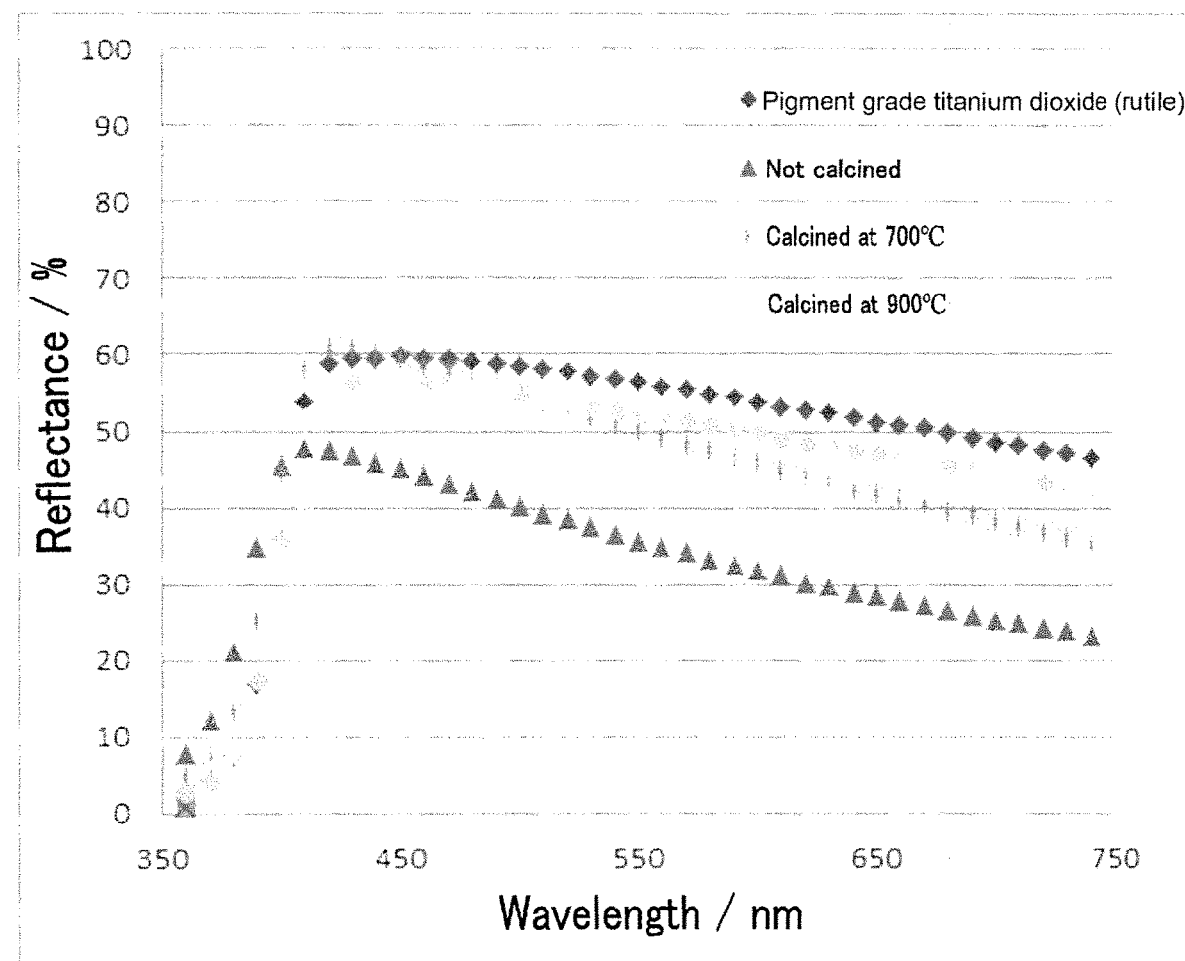
FIG. 2 shows the spectral reflectances of a rutile pigment grade titanium dioxide (*1), Titanium dioxide B (not calcined), and Titanium dioxide B calcined at 700 and 900° C.

Results of measurement of spectral reflectances of the rutile pigment grade titanium dioxide (*1) and Titanium dioxide B (not calcined, calcination temperature: 700° C., 900° C.) are shown in FIG. 2. The measurement was performed in such a manner that the titanium dioxide powder was dispersed and mixed into a nitrocellulose lacquer in a concentration of 5%, a resultant dispersion was applied to black and white concealing ability test charts in accordance with JIS-K5400 with a coating thickness of 0.101 μm and dried to prepare test samples, and using the prepared test samples, a colorimetric measurement was performed on each coating surface of a black portion of the charts with a spectrocolorimeter (CM-2600, manufactured by Konica Minolta, Inc.) to give the spectral reflectance.

Figure 3:
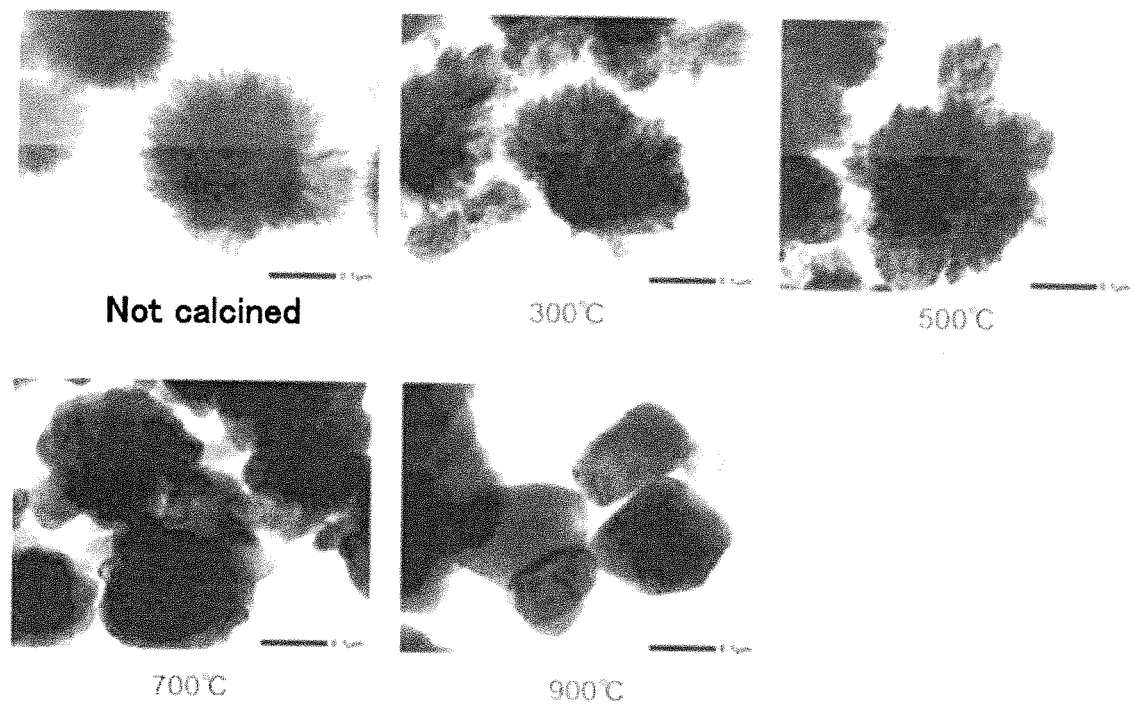
FIG. 3 is TEM observation showing a change in the shape of Titanium dioxide B at each calcination temperature.

With respect to Titanium dioxide B, TEM (transmission electron microscope) images were taken before and after the calcination (calcination temperature: 300° C., 500° C., 700° C., 900° C.). The results are shown in FIG. 3.

Figure 4:
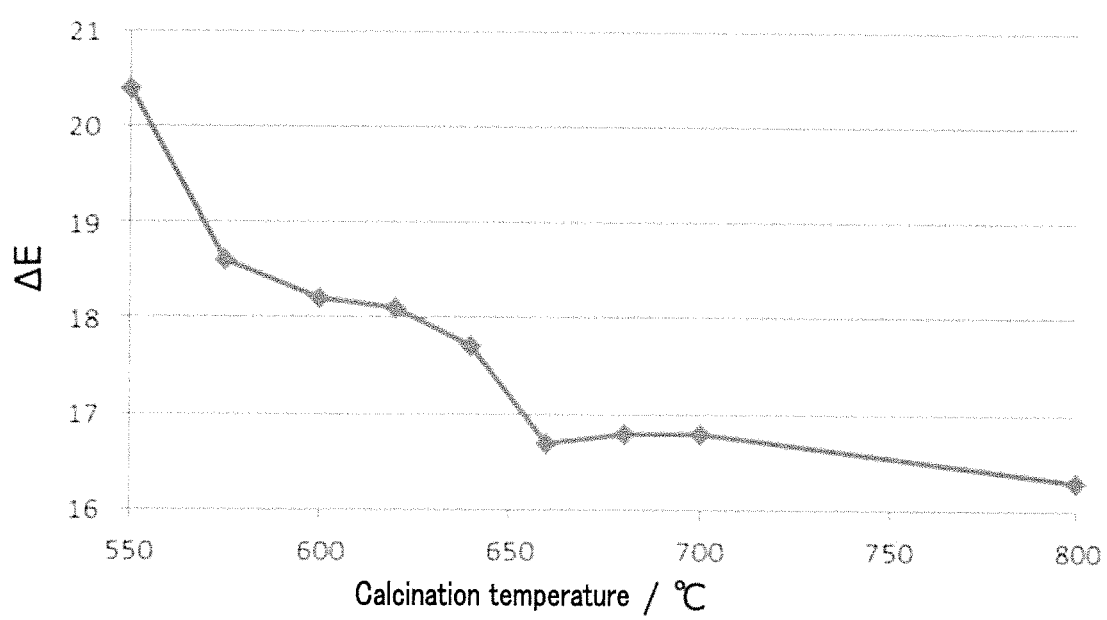
FIG. 4 shows a change in the concealing ability of Titanium dioxide B according to a change in the calcination temperature of a rotary kiln.
Figure 5:
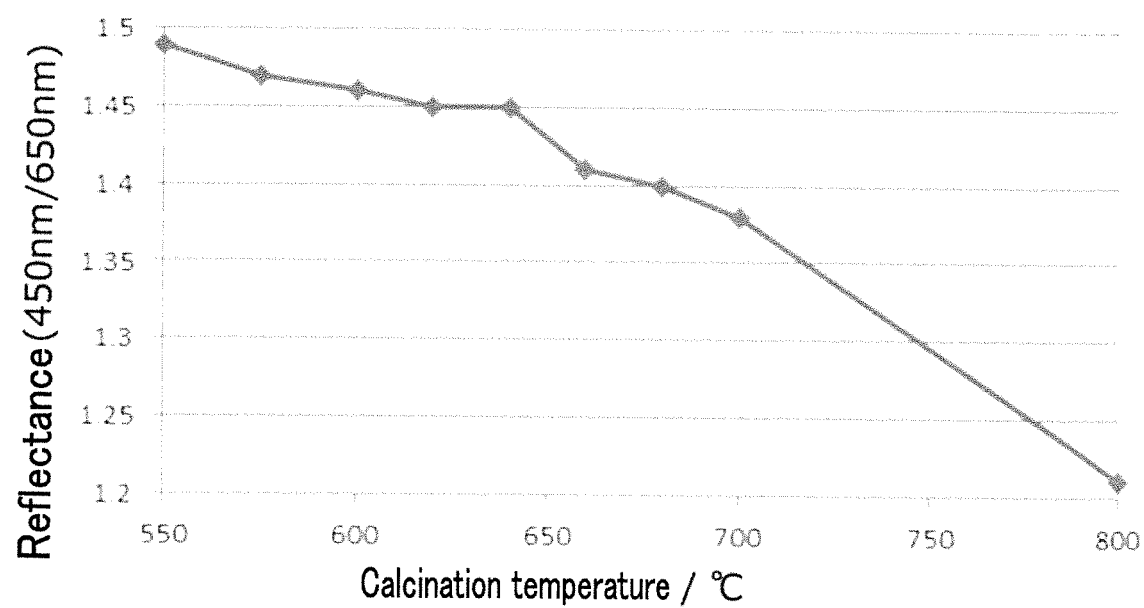
FIG. 5 shows a change in the red-light transmittance of Titanium dioxide B according to a change in the calcination temperature of a rotary kiln

Furthermore, the concealing ability and the red-color transmitting property according to changes in the calcination temperature were measured for Titanium dioxide B. The results are shown in FIG. 4 and FIG. 5, respectively.

Based on the above results, when the calcination is performed in the muffle furnace, an appropriate temperature range is from 500 to 800° C., and more desirably from 500 to 700° C.

Next, the present inventors investigated on the calcination temperature ranging from 500° C. to 800° C. in detail using Titanium dioxide B as a mother nucleus. That is, the present inventors evaluated a titanium dioxide powder calcined at various calcination temperatures by the above evaluation methods. The results are shown in Tables 5 and 6.

The calcination was performed in a rotary calcination furnace (rotary kiln) which allows a production close to a mass production with high calcination efficiency.

It is known that the rotary calcination furnace generally has a high calcination efficiency and can provide the same calcination state as calcination performed in a static muffle furnace, with a lower temperature.

TABLE 9

| Calcination temperature | 0 | 550 | 575 | 600 | 620 | 640 |
|---|---|---|---|---|---|---|
| Ratio between minor axis and major axis | 1.4 | 1.4 | 1.4 | 1.4 | 1.4 | 1.4 |
| Average Crystallite size nm | 11 | 17 | 19 | 20 | 21 | 22 |
| Specific surface area | 117 | 21 | 20 | 18 | 18 | 17 |
| Concealing ability (ΔE (Hunter)) | 34.0 | 20.4 | 18.6 | 18.2 | 18.1 | 17.7 |
| Concealing ability evaluation | C | B | A | A | A | A |
| R450/R650 | 1.57 | 1.49 | 1.47 | 1.46 | 1.45 | 1.45 |
| Red-color transmitting property evaluation | A | A | A | A | A | A |

TABLE 10

| Calcination temperature | 660 | 680 | 700 | 800 |
|---|---|---|---|---|
| Ratio between minor axis and major axis | 1.4 | 1.4 | 14 | 1.3 |
| Average Crystallite size nm | 24 | 27 | 29 | 33 |
| Specific surface area | 16 | 15 | 14 | 9 |
| Concealing ability (ΔE (Hunter)) | 16.7 | 16.8 | 16.8 | 16.3 |
| Concealing ability evaluation | A | A | A | A |
| R450/R650 | 1.41 | 1.4 | 1.38 | 1.21 |
| Red-color transmitting property evaluation | A | B | B | D |

The specific surface area is an index that shows a reduction in voidage and a progression of the sintering of the obtained titanium dioxide particles. In the titanium dioxide used in the present invention, the specific surface area thereof becomes preferably within a range of 8 to 30% compared to that of before the calcination (100%) by calcining titanium dioxide powder used as a mother nucleus.

Based on these results, it was found that in order to obtain excellent concealing ability and red-color transmitting property, the calcination temperature is preferably 550 to 700° C., and more preferably 575 to 660° C.

[Solid Powder Cosmetic]

Further, the present inventors used the titanium dioxide produced at the calcination temperature of 660° C. in Table 6 to prepare, in a usual manner, a solid powder cosmetic blended with a hydrophobized titanium dioxide produced by the surface treatment method below. The produced cosmetics were evaluated by the evaluation method below.

[Surface Treatment Method of Titanium Dioxide Powder]

The produced titanium dioxide powder was dispersed to ion-exchanged water, which was heated and then made to adsorb 3% by mass of stearic acid. Then, the resultant was dehydrated, washed, and dried to produce a surface-treated titanium dioxide.

[Production Method of Solid Powder Cosmetic]
<Dry Production Method>

An inorganic powder component, an oily component, and other components were mixed by a Henschel mixer to be crushed by a pulverizer for two times. Then, the obtained mixture was filled in an inner plate type container made of resin and subjected to a dry press molding by a well-known method to give a solid powder cosmetic blended with titanium dioxide of the present invention.

<Other Production Methods>

Well-known methods can be used as the production method of blending titanium dioxide of the present invention to the cosmetic. For example, the production method of preparing the cosmetic by drying a slurry that uses a volatile solvent described in Japanese Patent No. 5422092, or the production method of preparing the cosmetic by removing a slurry that uses a volatile solvent after filling described in Japanese Patent No. 5972437 can be used preferably.

[Evaluation Method of Solid Powder Cosmetic]

Evaluation (6): Natural Makeup Finish 10 trained-expert panelists applied the sample to their faces and evaluated feeling in use after application.

A: 7 or more out of 10 panelists answered that a makeup finish was natural.

B: 5 or more to less than 7 out of 10 panelists answered that a makeup finish was natural.

C: less than 5 out of 10 panelists answered that a makeup finish was natural.

Evaluation (7): Spreadability 10 trained-expert panelists applied the sample to their faces and evaluated feeling in use after application.

A: 7 or more out of 10 panelists answered that spreadability was good.

B: 5 or more to less than 7 out of 10 panelists answered that spreadability was good.
C: less than 5 out of 10 panelists answered that spreadability was good.

Evaluation (8): Unnatural Whiteness 10 trained-expert panelists applied the sample to their faces and evaluated feeling in use after application.
A: 7 or more out of 10 panelists answered that there was no unnatural whiteness.
B: 5 or more to less than 7 out of 10 panelists answered that there was no unnatural whiteness.
C: less than 5 out of 10 panelists answered that there was no unnatural whiteness.

Evaluation (9): Covering of Pigmented Spots and Freckles 10 trained-expert panelists applied the sample to their faces and evaluated feeling in use after application.
A: 7 or more out of 10 panelists answered that pigmented spots and freckles were covered.
B: 5 or more to less than 7 out of 10 panelists answered that pigmented spots and freckles were covered.
C: less than 5 out of 10 panelists answered that pigmented spots and freckles were covered.

Evaluation (10): Noticeableness of Skin Texture 10 trained-expert panelists applied the sample to their faces and evaluated feeling in use after application.
A: 7 or more out of 10 panelists answered that skin texture was not noticeable.
B: 5 or more to less than 7 out of 10 panelists answered that skin texture was not noticeable.
C: less than 5 out of 10 panelists answered that skin texture was not noticeable.

Evaluation (11): Color Unevenness 10 trained-expert panelists applied the sample to their faces and evaluated feeling in use after application.
A: 7 or more out of 10 panelists answered that there was no color unevenness.
B: 5 or more to less than 7 out of 10 panelists answered that there was no color unevenness.
C: less than 5 out of 10 panelists answered that there was no color unevenness.

TABLE 11

| Test Example | 8-1 | 8-2 | 8-3 | 8-4 | 8-5 | 8-6 | 8-7 | 8-8 | 8-9 |
|---|---|---|---|---|---|---|---|---|---|
| Silicone-treated talc *1 | to 100% | to 100% | to 100% | to 100% | to 100% | to 100% | to 100% | to 100% | to 100% |
| Synthetic fluorine phlogopite iron (particle size: 6 μm) *2 | 30 | | | 30 | 30 | | | | 30 |
| Synthetic fluorine phlogopite (particle size: 7 μm) *3 | | 30 | | | | 30 | | | |
| Synthetic fluorine phlogopite (particle size: 12 μm) *4 | | | 30 | | | | 30 | | |
| Synthetic fluorine phlogopite (particle size: 20 μm~) *5 | | | | | | | | 30 | |
| Sericite *6 | | | | | | | | | 7 |
| Boron nitride *7 | 7 | 7 | 7 | 7 | 7 | 7 | 7 | 7 | |
| Pigment grade titanium dioxide *8 | | | | | 9 | 9 | 9 | | |
| Titanium dioxide of the present invention (calcined) | 9 | 9 | 9 | | | | | 9 | 9 |
| Titanium dioxide (not calcined) | | | | 9 | | | | | |
| Fine-particle titanium dioxide *9 | 3 | 3 | 3 | 3 | 3 | 3 | 3 | 3 | 3 |
| Silicone-treated colcothar *10 | 0.3 | 0.3 | 0.3 | 0.3 | 0.3 | 0.3 | 0.3 | 0.3 | 0.3 |
| Silicone-treated yellow iron oxide *11 | 1.5 | 1.5 | 1.5 | 1.5 | 1.5 | 1.5 | 1.5 | 1.5 | 1.5 |
| Silicone-treated black iron oxide *12 | 0.2 | 0.2 | 0.2 | 0.2 | 0.2 | 0.2 | 0.2 | 0.2 | 0.2 |
| Spherical dimeticone/vinyl dimethicone crosspolymer *13 | 6 | 6 | 6 | 6 | 6 | 6 | 6 | 6 | 6 |
| Spherical nylon powder *14 | 10 | 10 | 10 | 10 | 10 | 10 | 10 | 10 | 10 |
| Zinc oxide | 2 | 2 | 2 | 2 | 2 | 2 | 2 | 2 | 2 |
| Pearl (mica titanium) | 0.1 | 0.1 | 0.1 | 0.1 | 0.1 | 0.1 | 0.1 | 0.1 | 0.1 |
| Paraben (antiseptic agent) | suitable amount | suitable amount | suitable amount | suitable amount | suitable amount | suitable amount | suitable amount | suitable amount | suitable amount |
| Semisolid silicone oil | 0.2 | 0.2 | 0.2 | 0.2 | 0.2 | 0.2 | 0.2 | 0.2 | 0.2 |
| Silicone oil | 3 | 3 | 3 | 3 | 3 | 3 | 3 | 3 | 3 |
| Ester oil | 2 | 2 | 2 | 2 | 2 | 2 | 2 | 2 | 2 |
| Ethylhexyl p-methoxycinnamate | 4 | 4 | 4 | 4 | 4 | 4 | 4 | 4 | 4 |
| Anti-oxidant | suitable amount | suitable amount | suitable amount | suitable amount | suitable amount | suitable amount | suitable amount | suitable amount | suitable amount |
| Total | 100 | 100 | 100 | 100 | 100 | 100 | 100 | 100 | 100 |

TABLE 11-continued

| Test Example | 8-1 | 8-2 | 8-3 | 8-4 | 8-5 | 8-6 | 8-7 | 8-8 | 8-9 |
|---|---|---|---|---|---|---|---|---|---|
| Natural makeup finish | A | A | A | A | B | B | B | A | A |
| Spreadability | A | A | A | A | A | A | A | A | C |
| Unnatural whiteness | A | A | A | A | C | C | C | A | A |
| Covering of pigmented spots and freckles | A | A | A | C | A | A | A | A | A |
| Noticeableness of skin texture | A | A | A | B | A | A | A | B | A |
| Color unevenness | A | A | A | A | A | A | A | B | A |

TABLE 12

| Test Example | 8-10 | 8-11 | 8-12 | 8-13 |
|---|---|---|---|---|
| Silicone-treated talc *1 | to 100% | to 100% | to 100% | to 100% |
| Synthetic fluorine phlogopite iron (particle size: 6 μm) *2 | 15 | 15 | | |
| Synthetic fluorine phlogopite (particle size: 7 μm) *3 | | | 15 | 15 |
| Synthetic fluorine phlogopite (particle size: 12 μm) *4 | | | | |
| Synthetic fluorine phlogopite (particle size: 20 μm~) *5 | | | | |
| Sericite *6 | 7 | 7 | | |
| Boron nitride *7 | 25 | 0.2 | 7 | 7 |
| Pigment grade titanium dioxide *8 | | | | |
| Titanium dioxide of the present invention (calcined) | 9 | 9 | 0.5 | 32 |
| Titanium dioxide (not calcined) | | | | |
| Fine-particle titanium dioxide *9 | 3 | 3 | 3 | 3 |
| Silicone-treated colcothar *10 | 0.3 | 0.3 | 0.3 | 0.3 |
| Silicone-treated yellow iron oxide *11 | 1.5 | 1.5 | 1.5 | 1.5 |
| Silicone-treated black iron oxide *12 | 0.2 | 0.2 | 0.2 | 0.2 |
| Spherical dimeticone/vinyl dimethicone crosspolymer *13 | 6 | 6 | 6 | 6 |
| Spherical nylon powder *14 | 10 | 10 | 10 | 10 |
| Zinc oxide | 2 | 2 | 2 | 2 |
| Pearl (mica titanium) | 0.1 | 0.1 | 0.1 | 0.1 |
| Paraben (antiseptic agent) | suitable amount | suitable amount | suitable amount | suitable amount |
| Semisolid silicone oil | 0.2 | 0.2 | 0.2 | 0.2 |
| Silicone oil | 3 | 3 | 3 | 3 |
| Ester oil | 2 | 2 | 2 | 2 |
| Ethylhexyl p-methoxycinnamate | 4 | 4 | 4 | 4 |
| Anti-oxidant | suitable amount | suitable amount | suitable amount | suitable amount |
| Total | 100 | 100 | 100 | 100 |
| Natural makeup finish | B | A | B | B |
| Spreadability | A | C | A | A |
| Unnatural whiteness | A | A | A | C |
| Covering of pigmented spots and freckles | A | A | C | A |
| Noticeableness of skin texture | C | A | A | A |
| Color unevenness | A | A | A | A |

*1 SA-TALC JA-68R, manufactured by Miyoshi Kasei, Inc.
*2 PDM-FE, manufactured by Topy Industries, Ltd.
*3 PDM-5L, manufactured by Topy Industries, Ltd.
*4 PDM-10L, manufactured by Topy Industries, Ltd.
*5 PDM-20L, manufactured by Topy Industries, Ltd.
*6 Sericite FSE, manufactured by Sanshin Mining Ind. Co., Ltd.
*7 RonaFlair Boroneige SF-12, manufactured by Merck KGaA
*8 TIPAQUE, manufactured by ISHIHARA SANGYO KAISHA, LTD.
*9 MT-100TV, manufactured by Tayca Corporation
*10 OTS-2 colcothar No. 216P, manufactured by DAITO KASEI KOGYO CO., LTD.
*11 OTS-2 STN-1, manufactured by DAITO KASEI KOGYO CO., LTD.
*12 OTS-2 BL-100, manufactured by DAITO KASEI KOGYO CO., LTD.
*13 TORAYFIL E-506S, manufactured by Dow Corning Toray Co., Ltd.
*14 NYLON SP-500, manufactured by Toray Industries, Inc.

From Test examples 8-1 to 8-3, it was found that the solid powder cosmetic produced with the titanium dioxide of the present invention, boron nitride and synthetic fluorine phlogopite or synthetic fluorine phlogopite iron is excellent in texture and makeup finish, and provides natural makeup finish and no unnatural whiteness upon application to skin.

From Test example 8-4, it was found that when the titanium dioxide used in a mother nucleus is used as it is, it is inferior in terms of covering of pigmented spots and freckles and noticeableness of skin texture.

From Test examples 8-5 to 8-7, it was found that when the conventional pigment grade titanium is used, it is inferior in terms of non-unnatural whiteness upon application to skin.

From Test example 8-8, it was found that even if the titanium dioxide of the present invention and boron nitride are used, it is inferior in terms of color unevenness and noticeableness of skin texture when the particle size of synthetic fluorine phiogopite exceeds 20 μm.

From Test example 8-9, it was found that when the titanium dioxide of the present invention is mixed by sericite instead of boron nitride, it is inferior in terms of spreadability.

From Test example 8-10, it was found that when the amount of boron nitride is larger than the range of the present invention, noticeableness of skin texture is emphasized and makeup finish is inferior.

From Test example 8-11, it was found that when the amount of boron nitride is smaller than the range of the present invention, it is inferior in terms of spreadability.

From Test example 8-12, it was found that when the amount of titanium dioxide of the present invention is smaller than the range of the present invention, it is inferior in terms of covering of pigmented spots and freckles, and a natural makeup finish cannot be achieved.

From Test example 8-13, it was found that when the amount of titanium dioxide of the present invention is larger than the range of the present invention, it is inferior in terms of natural makeup finish and non-unnatural whiteness.

What is claimed is:

1. A titanium dioxide powder, wherein:
    said titanium dioxide powder is a plurality of particles, each particle having radially projected needle projections coagulated, and
    said particle further comprising:
        an apparent average particle size that is not less than 100 nm and less than 500 nm;
        an average crystallite size that is in a range of 15 to 30 nm;
        a specific surface area that is in a range of 10 to 30 m$^2$/g; and
        a ratio between a minor axis and a major axis (major axis/minor axis) of said particle is not less than 1.0 and less than 2.5, and
    wherein said average crystallite size is measured using an X-ray diffractometry.

2. The titanium dioxide powder, according to claim 1, wherein:
said ratio between said minor axis and said major axis (major axis/minor axis) is in a range of 1.0 to 2.0.

3. A powder cosmetic, comprising:
1 to 30% by mass of said powder cosmetic of a titanium dioxide powder;
1 to 20% by mass of said powder cosmetic of a boron nitride; and
10 to 50% by mass of said powder of a layered plate silicate; and
said titanium dioxide powder is a plurality of particles, each particle having radially projected needle projections coagulated, and
said particle further comprising:
an apparent average particle size that is not less than 100 nm and less than 500 nm;
an average crystallite size that is in a range of 15 to 30 nm; and
a specific surface area that is in a range of 10 to 30 m$^2$/g;
wherein said average crystallite size is measured using an X-ray diffractometry.

4. A powder cosmetic, comprising:
1 to 30% by mass of said powder cosmetic of a rutile titanium dioxide powder;
1 to 20% by mass of said powder cosmetic of a boron nitride;
10 to 50% by mass of said powder cosmetic of a layered plate silicate; and
said rutile titanium dioxide powder, further comprising
an average crystallite size that is in a range of 15 to 30 nm;
a specific surface area that is in a range of 10 to 30 m$^2$/g;
a reflectance at 450 nm that is 1.3 times larger or more than a reflectance at 650 nm; and
a color difference (ΔE) that is not more than 22;
wherein said average crystallite size is measured using an X-ray diffractometry, and said color difference (ΔE) of said rutile titanium dioxide powder is obtained using a method comprising steps of:
dispersing and mixing said rutile titanium dioxide powder in a nitrocellulose lacquer to make a 5% concentration;
applying an obtained dispersion to make a coating having a thickness of 0.101 μm on a black-and-white concealing level test chart, JIS-K5400;
drying to prepare a test sample;
measuring a color of each coating surface of a white paper and a black paper of said test sample using a spectrocolorimeter; and
calculating said color difference (ΔE) based on a Hunter Lab color space.

5. A powder cosmetic, comprising:
1 to 30% by mass of said powder cosmetic of a titanium dioxide powder;
1 to 20% by mass of said powder cosmetic of a boron nitride; and
10 to 50% by mass of said powder cosmetic of a layered plate silicate; and
said titanium dioxide powder further comprising:
an apparent average particle size that is not less than 100 nm and less than 500 nm;
an average crystallite size is in a range of 15 to 30 nm; and
a specific surface area is in a range of 10 to 30 m$^2$/g;
wherein said titanium dioxide powder is a calcined second rutile titanium dioxide powder that is obtained by calcinating a first rutile titanium dioxide, said first rutile titanium dioxide having needle particles radially orientated and aggregated and needle projections on a particle surface thereof and further comprising:
(a) an apparent average particle size that is not less than 100 nm and less than 500 nm;
(b) an average crystallite size is in a range of 1 to 25 nm; and
(c) a specific surface area is in a range of 40 to 200 m$^2$/g;
wherein said average crystallite size is measured by an X-ray diffractometry.

6. A powder cosmetic, comprising:
1 to 30% by mass of said powder cosmetic of a titanium dioxide powder;
1 to 20% by mass of said powder cosmetic of a boron nitride;
10 to 50% by mass of said powder cosmetic of a layered plate silicate; and
wherein said titanium dioxide powder is a calcined second rutile titanium dioxide powder that is obtained by calcinating a first rutile titanium dioxide having needle projections on a particle surface thereof and further comprising:
(a) an apparent average particle size that is not less than 100 nm and less than 500 nm;
(b) an average crystallite size is in a range of 1 to 25 nm;
(c) a specific surface area is in a range of 40 to 200 m$^2$/g; and
wherein a specific surface area of said calcined second rutile titanium dioxide powder particle is in a range of 8% to 50% of a specific surface area of said first rutile titanium dioxide; and said average crystallite size is measured using an X-ray diffractometry.

7. The powder cosmetic, according to claim 5, wherein:
a calcination temperature of said first rutile titanium dioxide is from 500 to 800° C.

8. The powder cosmetic, according to claim 7, wherein:
said calcination temperature of said first rutile titanium dioxide is from 550 to 750° C.

9. The powder cosmetic, according to claim 3, wherein:
an aspect ratio of said layered plate silicate is in a range of 30 to 80.

10. The powder cosmetic, according to claim 3, wherein:
an average particle size of said layered plate silicate is in a range of 2 to 20 μm.

* * * * *